United States Patent
Marshall et al.

(10) Patent No.: US 8,343,109 B2
(45) Date of Patent: Jan. 1, 2013

(54) MULTI-SPRING SUPPORT FOR NEEDLE SYRINGES

(75) Inventors: Jeremy Marshall, Jericho (GB); David Danvers Crossman, Christmas Common (GB)

(73) Assignee: Owen Mumford Limited, Jericho (GB)

( * ) Notice: Subject to any disclaimer, the term of this patent is extended or adjusted under 35 U.S.C. 154(b) by 1336 days.

(21) Appl. No.: 10/506,472

(22) PCT Filed: Mar. 5, 2003

(86) PCT No.: PCT/GB03/00902
§ 371 (c)(1),
(2), (4) Date: Apr. 6, 2005

(87) PCT Pub. No.: WO03/074111
PCT Pub. Date: Sep. 12, 2003

(65) Prior Publication Data
US 2005/0165361 A1    Jul. 28, 2005

(30) Foreign Application Priority Data
Mar. 5, 2002 (GB) .................................. 0205066.4

(51) Int. Cl.
*A61M 5/32* (2006.01)
(52) U.S. Cl. ........................................... 604/198
(58) Field of Classification Search .......... 604/134–136, 604/157, 187, 195–198
See application file for complete search history.

(56) References Cited

U.S. PATENT DOCUMENTS

| 3,403,679 | A | | 10/1968 | Watson et al. | |
|---|---|---|---|---|---|
| 4,858,607 | A | * | 8/1989 | Jordan et al. | 606/182 |
| 5,599,309 | A | | 2/1997 | Marshall et al. | |
| 5,879,311 | A | * | 3/1999 | Duchon et al. | 600/583 |
| 6,270,479 | B1 | * | 8/2001 | Bergens et al. | 604/156 |

FOREIGN PATENT DOCUMENTS

| EP | 0 516 473 | 12/1992 |
|---|---|---|
| GB | 906 574 | 9/1962 |

* cited by examiner

*Primary Examiner* — Kevin C Sirmons
*Assistant Examiner* — Andrew Gilbert
(74) *Attorney, Agent, or Firm* — Young & Thompson

(57) ABSTRACT

When a trigger of an injection device is released, a main spring (4) expands, driving a member (7) forwards. This compresses a weak spring (11), but a spring (5) is stiff enough to remain expanded. A syringe (2) is thus thrust forwards via a collar (9), so that a needle (3) projects from a barrel (1). The spring (4) continues to expand after the syringe has reached its forward position, with the spring (11) fully compressed, so that the stem (8) of the member (7) acts on a piston (14) within the syringe (2), to expel the dose while the spring (5) is caused to be compressed. The spring (5) ensures that the syringe is retained in its forward position during this phase.

5 Claims, 1 Drawing Sheet

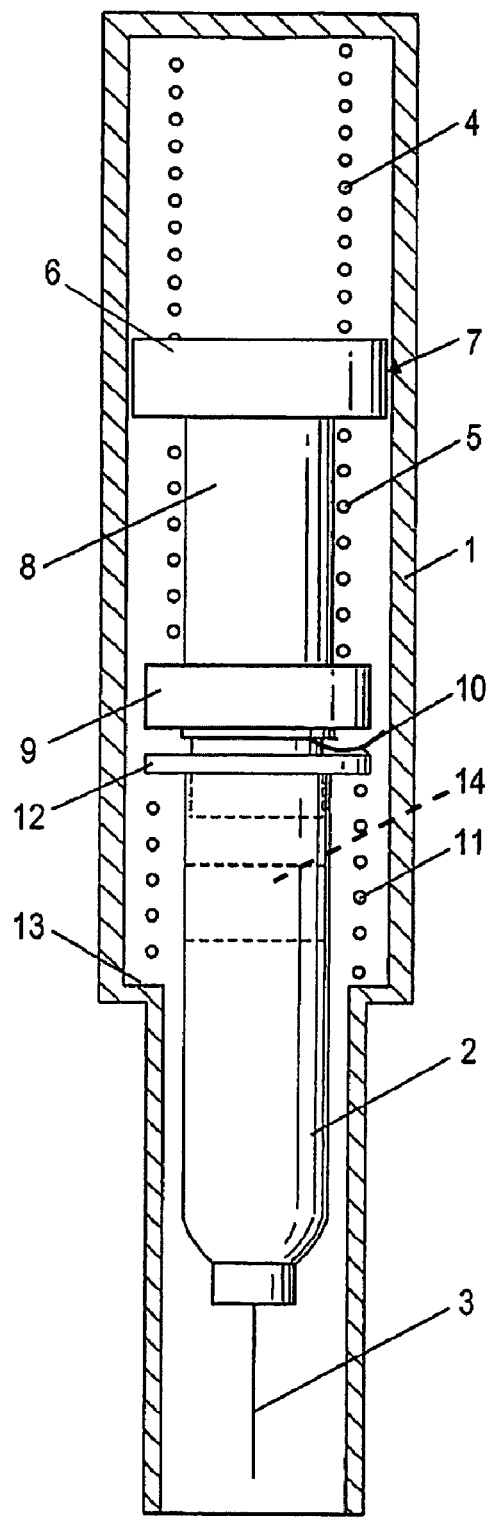

MULTI-SPRING SUPPORT FOR NEEDLE SYRINGES

This invention relates to injection devices. It is concerned with those devices for medical use where a syringe is loaded into a firing mechanism which first thrusts the syringe forwards to project the needle, and then acts on the piston within the syringe to express the dose.

It is well known to use a single drive spring which, when released, acts on a plunger directly connected to the piston of the syringe. The incompressiblity of the dose and the fineness of the needle bore means that the syringe is thrust forwards by the force on its piston. But once the needle is projected the syringe is arrested while the drive spring continues to act to expel the dose through the needle. There is sometimes a return spring which acts between the syringe and the housing and which is compressed as the syringe moves forwards.

Certain syringes have large needles which require substantial force to make then penetrate. Also there have been developed low friction bungs or pistons for syringes, making it easier to expel a dose. With a combination of a large needle and a low friction piston, and with the single drive spring technique described above, there will be a tendency for the piston to start moving forwards within the syringe before the needle has fully penetrated. The dose will therefore start to be delivered whilst the tip of the needle is still moving into the flesh, and not all of the intended dose will be ejected at the correct depth.

It is therefore desirable for this "pre-drip" to be eliminated as far as possible, which is what the proposal described below seeks to do.

According to the present invention there is provided an injection device having a housing with a spring drive releasable sequentially firstly to urge a syringe within the housing forwards to project its needle from the forward end of the housing and then to press a piston within the syringe forwards to eject a dose through the needle, wherein the spring drive includes a first spring that acts between the housing and a plunger aligned to co-operate with the piston, and a second spring that acts between, the plunger and the syringe, the second spring being weaker than the first spring but being sufficiently stiff to be in an expanded state when the syringe reaches its forward position with its needle penetrating the flesh of a patient, whereupon the first spring, as it fully expands, will then compress the second spring to urge the plunger forwards and thereby move the piston and expel the dose within the syringe, the second spring meanwhile serving to retain the syringe seated at its forward position.

Thus the piston is not acted upon until the needle has penetrated.

It is unlikely that the second spring will act directly on the syringe. Instead, the plunger may have a collar slidable lengthwise within limits, and the second spring will bear on the rear side of this collar, while the forward side of the collar co-operates with the syringe.

To keep the syringe in place initially there may be a third, light spring urging the syringe rearwardly so that its needle is retracted within the housing prior to use. Conveniently this spring encircles the syringe and acts between a rear flange of the syringe and an internal shoulder of the housing. Although it becomes compressed during the injection process it will not be powerful enough to affect the action of the first and second springs, nor will it cause the syringe to retract after use.

For a better understanding of the invention, one embodiment will now be described, by way of example, with reference to the accompanying drawing, in which the single FIGURE is a diagrammatic axial section of an injection device.

The device has a barrel 1 which can house a syringe 2 at its forward end. The syringe is movable axially of the barrel between a position in which its needle 3 is retracted and a position in which that needle projects a set distance.

The forward drive for the syringe, which first moves the syringe body and then urges its piston forwards to expel the dose, consists of two springs 4 and 5 in tandem. The rear spring 4 is the more powerful and acts between the rear end of the barrel and the head 6 of a mushroom shaped member 7 whose stem 8 extends forwardly and can enter the rear end of the syringe 2. The second spring 5, through which the stem 8 extends, acts between the head 6 and a collar 9 slideable along the stem but limited in the forward direction by a circlip 10. A further light spring 11 acts in the rearward direction on the rear flange 12 of the syringe, the spring 11 encircling the syringe body and reacting against an inward shoulder 13 of the barrel 1. The release trigger for the drive spring 4 is not shown for simplicity.

Initially, the syringe is retracted, and the main spring 4 is held compressed. Although shown slightly apart, the collar 9 and syringe flange 12 will be closed together, and there is a balance between the springs 5 and 11 that holds the syringe in place.

When the trigger is released and the device is fired, the main spring 4 expands, driving the member 7 forwards. The spring 5 is stiff enough and the spring 11 weak enough for the spring 5 to remain expanded, and to thrust the syringe 2 forwards via the collar 9, so that the needle 3 projects from the barrel 1. The spring 4 continues to expand after the syringe has reached its forward position, with the spring 11 fully compressed, so that the stem 8 of the member 7 acts on a bung 14, acting as a piston within the syringe 2, to expel the dose while the spring 5 is caused to be compressed. The spring 5 ensures that the syringe is retained in its forward position during this phase.

When the spring 4 is fully expanded, the injection is complete and the device is withdrawn from the patient with the needle 3 still projecting.

The invention claimed is:

1. An injection device comprising:
   a housing having a forward end and a rearward end;
   a syringe having a needle and containing a dose for being ejected through said needle by means of a piston slideable within the syringe, said syringe being moveable within the housing to a forward position to project its needle from the forward end of the housing;
   a spring drive operable firstly to urge the syringe to its forward position and then to press said piston to eject said dose, said drive including:
   a first spring acting between the housing and a plunger aligned to cooperate with the piston to urge the piston forwardly, and
   a second spring acting in compression between said plunger and the syringe and in opposition to said first spring when the plunger presses said piston forwards to eject the dose,
   the second spring being weaker than the first spring but being sufficiently stiff to be in an expanded state when the syringe reaches its forward position with its needle penetrating the flesh of a patient, whereupon the first spring, as it fully expands, will then compress the second spring to urge the plunger forward and thereby move the piston and expel a dose from the syringe, the second spring meanwhile serving to retain the syringe seated at its forward position, whereby said piston is not acted upon until the needle has penetrated.

2. The injection device of claim 1, further comprising a third, light spring urging the syringe rearwardly so that its needle is retracted within the housing prior to use.

3. The injection device of claim 1, wherein the ejection of said dose is caused by further expansion of said first spring and is accompanied by compression of said second spring throughout the stroke of movement of said piston.

4. The injection device of claim 1, wherein during initial expansion movement of said first spring, said piston is isolated from the thrust of said first spring solely by the opposing force of the second spring.

5. The injection device of claim 1, wherein the first spring contacts the plunger and the housing, and the second spring contacts the plunger and the syringe.

* * * * *